United States Patent [19]
Bergner et al.

[11] Patent Number: 6,149,272
[45] Date of Patent: Nov. 21, 2000

[54] ARRANGEMENT FOR PROJECTING A TWO-DIMENSIONAL IMAGE ONTO AN EYE TO BE EXAMINED FOR USE WITH A DEVICE THAT PERFORMS A SUBJECTIVE DETERMINATION OF REFRACTION AND/ OR A DEVICE THAT PERFORMS OTHER VISION FUNCTIONS

[75] Inventors: Roland Bergner; Klaus-Ditmar Voigt, both of Jena, Germany

[73] Assignee: Carl Zeiss Jena GmbH, Jena, Germany

[21] Appl. No.: 08/880,076

[22] Filed: Jun. 20, 1997

[30] Foreign Application Priority Data

Feb. 5, 1997 [DE] Germany .......................... 197 04 197

[51] Int. Cl.[7] ....................................................... A61B 3/10

[52] U.S. Cl. ............................ 351/221; 351/205; 351/211

[58] Field of Search ..................................... 351/205, 206, 351/210, 221, 222, 246, 158

[56] References Cited

U.S. PATENT DOCUMENTS

| | | | |
|---|---|---|---|
| 3,936,605 | 2/1976 | Upton | 351/50 |
| 4,768,873 | 9/1988 | Webb | 351/205 |
| 5,359,669 | 10/1994 | Shanley et al. | 351/205 |
| 5,430,505 | 7/1995 | Katz | 351/205 |
| 5,706,070 | 1/1998 | Reich et al. | 351/200 |

*Primary Examiner*—Huy Mai
*Attorney, Agent, or Firm*—Reed Smith Shaw & McClay LLP

[57] ABSTRACT

An arrangement for use with a device that determines subjective refraction and/or performs other visual functions, comprises at least one light source, at least one light modulator for modulating the light source to produce modulated light, a driving unit for controlling said modulator to modulate the light source in accordance with video information corresponding to a video image, a two-dimensional deflector for deflecting the modulated light to produce a two-dimensional image, an optical transmitter for optically transmitting the light of the light source, and an optical projector for optically projecting the two-dimensional image onto a retina of an eye to be examined.

13 Claims, 11 Drawing Sheets

ARRANGEMENT FOR PROJECTING A TWO-DIMENSIONAL IMAGE ONTO AN EYE TO BE EXAMINED FOR USE WITH A DEVICE THAT PERFORMS A SUBJECTIVE DETERMINATION OF REFRACTION AND/ OR A DEVICE THAT PERFORMS OTHER VISION FUNCTIONS

BACKGROUND OF THE INVENTION a) Field of the Invention

The invention relates to an arrangement for examination of vision functions, and, in particular, an arrangement for the subjective determination of refraction in the eye.

b) Description of the Related Art

There are various known spectacle type or helmet type frames which arrange screens in front of the eye of the observer or which reflect the image generated by screens or displays in front of the eye of the observer: U.S. Pat. No. 5,076,275, U.S. Pat. No. 4,361,384, U.S. Pat. No. 5,162,828, U.S. Pat. No. 4,869,575, Enhanced Vision. "V-max", brochure 800-440-9476, 1996. "Virtual displays" of this kind are sold by Virtual Research Systems, Inc. (FF5), for example.

U.S. Pat. No. 5,369,415 and EP 562,742 describe "direct retinal scan displays" in which only very low outputs (not more than 20 microwatts) are required owing to direct "writing" of the image information on the fundus oculi of the observer. Video information (e.g., RGB signals) is modulated on one or more laser beams and the latter is/are deflected in the x-direction and y-direction via scanners (e.g., piezo-crystals) and reflected into the observer's eye via a plane surface which can be spectacle glass. Variable optics serve to focus the beams on the retina.

U.S. Pat. No. 5,467,104 and WO 94/09472 describe a "virtual retina display" with high resolution and color representation. Light from lasers or LEDs is modulated, transmitted via light guides, and projected directly onto the retina by means of microscanners and projection optics. The reflecting element can also be a splitter mirror, so that the projected image is superimposed on the surroundings.

In WO 96/17562, a scanning unit is provided on a spectacle type frame and projects an image onto the retina via the reflecting spectacle lenses or glasses.

A "pupil tracking system" monitors the position of the eyes and displaces the projection direction so as always to strike the pupil of the observer. In DE 4091126, the patient views a screen through spectacles with liquid crystal shutters, on which screen are displayed symbols for binocular vision testing.

DE 4326760 C2 describes a device for testing central vision functions, preferably for perimetric examinations, wherein a light-proof or light-tight spectacle type carrier contains image-generating display screens for generating test marks or optotypes and an optical imaging system for compensation of refractive anomalies. The natural visual impression is impaired by the part of the spectacles arranged in front of the eyes which has screens in the viewing direction.

Examination instruments such as phoropters in which, e.g., spherical or cylindrical test glasses are swiveled in front of the eye to determine defective eyesight based on information from the test subject are known for determining subjective refraction and for determining other functions of the human eye. A disadvantage herein is that the test subject does not assume a relaxed posture and the natural visual impression is corrupted.

Therefore, arrangements have been developed to enable so-called "free-vision" refractive testing (U.S. Pat. No. 3,927,933, DE 2647848 A1, DD 293045 B5, DD 282851 B5, DD 273771 A1).

Further, test equipment for determining other functions of the human eye are known (OCULUS-Binoptometer, Binotest) to acquire information on the visual performance (e.g., color vision, stereo vision, driving vision) of the patient's eyes based on information given by the patient. These arrangements also have the disadvantage that they take up a relatively large amount of space and are poorly suited for mobile use, e.g., in developing countries. When used for testing defective vision of persons, especially for the first time, the test subject will often exhibit objective shyness of the medical equipment, which makes the examination difficult or even impossible.

OBJECT AND SUMMARY OF THE INVENTION

The primary object of the invention is therefore to improve and facilitate examination of defective vision and other visual functions.

In accordance with the invention, an arrangement for determining subjective refraction and/or for determining other visual functions, comprises at least one light source, a least one light modulator which follows the light source, a driving unit for controlling the modulator for modulating video information, two dimensional deflecting means for the light for generating an image, optical transmission means for transmitting the light of the light source and optical projection means for projecting the image onto the retina of the eye to be examined.

The invention can be used for testing the most important vision functions and for refractive determination in humans.

The very compact construction and wearing of light spectacles eliminates the need to look into a device. There is no more swiveling of large examination units (phoropters) in front of the eye. It is possible to superpose generated images on the surroundings in combination with a comfortable, relaxed sitting posture. The very high resolution which is made possible is coupled with low power consumption. There can be separate displays for the right eye and left eye, which is important for all binocular tests, wherein the disadvantages of other image-separating methods which partially determine function (color separation, polar separation, shutter principle, mechanical separators) can be eliminated.

In particular, the following functions can be tested according to the invention:

I.
Visual acuity (far, near, monocular, binocular), e.g., by means of the reflector (spectacle glass) with two zones:
a) the far part (image from infinity—e.g., plane mirror) and
b) the near part (image from defined distance, e.g., 40 cm—e.g., concave mirror).
All other test symbols can be generated; thus, a large selection is possible. Binocular testing is effected by a unit for each eye using the known adjustment possibilities of test spectacles and of eye tracking.
II.
Driving-related eye test
In this case, special testing processes are possible in accordance with the specifics of different nations.
III.
Stereopsis examination
Display of test images (different lateral disparity possible) which are offset laterally relative to one another by displacement of the scanned images. The lateral displacement path is calibrated in angle minutes stereopsis.

IV.

Phoria (angular vision deficiency)

Display of two separate images of different content. A displacement of these images on the retina of the test subject is made possible by displacement at the scanner or screen, wherein the displacement path can be calibrated in angular vision deficiency (prism diopters).

V.

Color vision test

When three light sources (RGB or RGY) are used, different color tests are possible (e.g., color charts; two fields analogous to the anomaloscope).

VI.

Visual field test

This test can be conducted in a manner analogous to the perimeter (full vision field or screening—central field, e.g., 30°).

The point of fixation is made in the center by a (blinking) dot.

The vision field test is carried out by dot display corresponding to preselectable program sequences.

VII.

Sensitivity to glare, dark adaptation

The blinding or dazzling of the eye is simulated by means of laterally disposed light sources; at the same time tests are performed which, in addition, can also be varied in contrast.

VII.

Contrast-dependent visual acuity

Tests can be carried out with different gray steps by modulating the intensity of the beams. The contrast ratios of the performed tests can accordingly be changed and a dependency of the detected visual acuity step upon contrast can be determined.

IX.

Objective refraction

Evaluation of the (preferably infrared) light reflected by the retina in a generally known autorefractor system. In cooperation with a retinal scan display, an alternative to the conventional phoropter/acuity projector/autorefractometer.

X.

Subjective refraction

A sharp imaging of the displayed images on the retina can be achieved through the intermediary of variable spherical and cylindrical optics. The adjustments of the optics can be calibrated and the refractive deficiency can accordingly be determined.

Testing prerequisites for the methods mentioned above in 1-X when using a retinal scan display are particularly the adjustment of the spectacles relative to the pair of eyes (pupil distance, height difference, corneal vertex difference)

a) automatic detection of the viewing direction of the eyes (tracking) and electrical tracking of the image b) manual or motor-driven adjusting possibility for test spectacles to ensure a defined display of the image on the respective optical axis of the eye of the test subject.

The reflector (spectacle glass) is constructed from different transparent materials depending on the kind of test:

a) full mirror (only image display)

b) partial mirror (superposition of image on surroundings)

The arrangements according to the invention can be used in different ways:

1. Use without additional optics—screening (mass screening)

The image will not be sharply imaged on the retina of a test subject with defective vision and test criteria are given without additional correction (e.g., detection of visual acuity 0.7), with reference to which a number of test subjects can be classed as "fail" or "pass", Those in the "fail" category must be examined further by a specialist.

2. Use with variable or exchangeable optics—determination of refraction, extensive examinations possible in that the image is sharply imaged on the retina when corrective optics are switched on or changed.

BRIEF DESCRIPTION OF THE DRAWINGS

In the following, the invention is explained further with reference to schematic drawings.

DESCRIPTION OF THE PREFERRED EMBODIMENTS

Figure 1A:
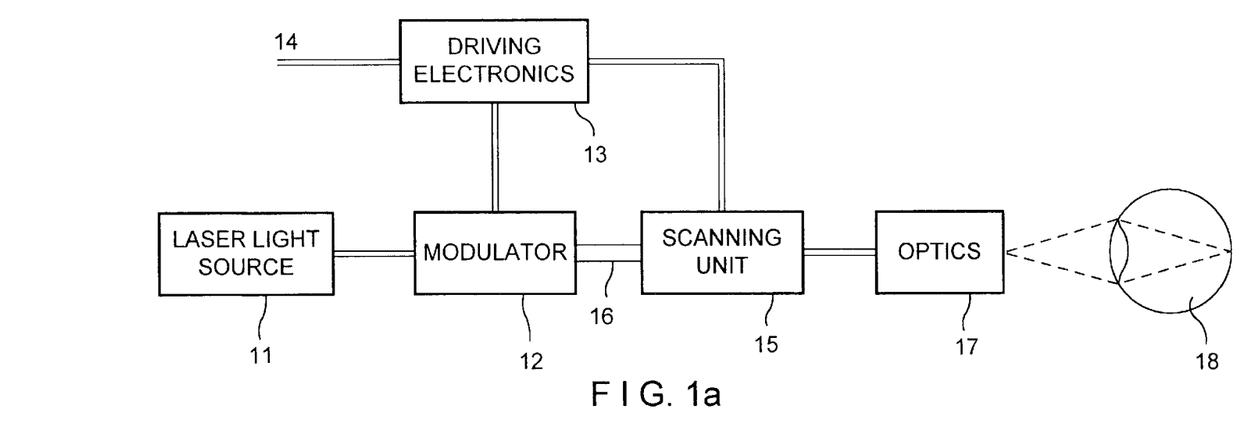
FIGS. 1a, b are schematic drawings of arrangements according to the invention.
Figure 1B:
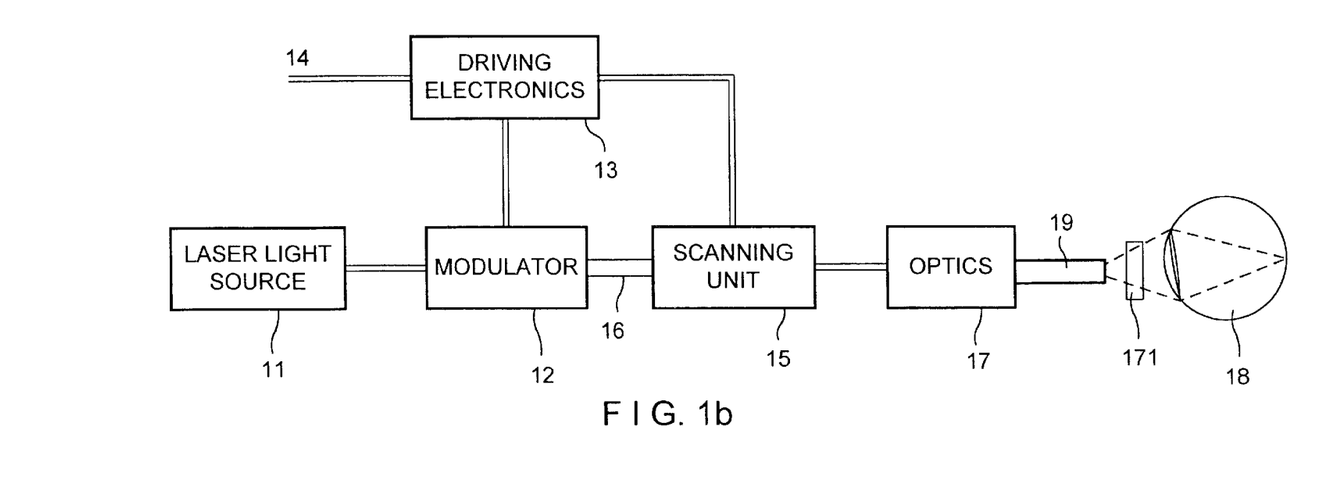

In FIGS. 1a, b, the light from one or more laser light sources 11 is brightness-modulated by a modulator 12 which is driven by driving electronics 13 which drive the modulator 12 and scanning unit 15 in accordance with the video signal 14 (e.g., RGB/RGY) present at their input. The brightness-modulated laser light reaches a two-dimensional scanning unit 15 either via a light-conducting fiber 16 according to FIG. 1a or directly as is shown in FIG. 1b. By means of two-dimensional deflection, the scanning unit 15 generates a video picture which is projected onto the retina, according to FIG. 1a, via variable optics 17 either via a reflector in accordance with FIGS. 2a and 2b of or by the optical system of the human eye 18 (cornea and lens) by means of direct projection which is not shown but is known per se from cited references. A signal train from the driver to the scanner ensures the required one-to-one geometrical correspondence of the image points of the video picture to the generated brightness steps of the modulator.

In FIG. 1b, the image generated by the scanning unit is advantageously fed into an image-carrying fiber bundle 19 via variable optics. The image formed at the output location of the image-carrying fiber bundle 19 is projected onto the retina via the eye lens. The sequence of scanning unit 15 and variable optics 17 in the beam path of the optical imaging can also be switched or exchanged.

Figure 2A:
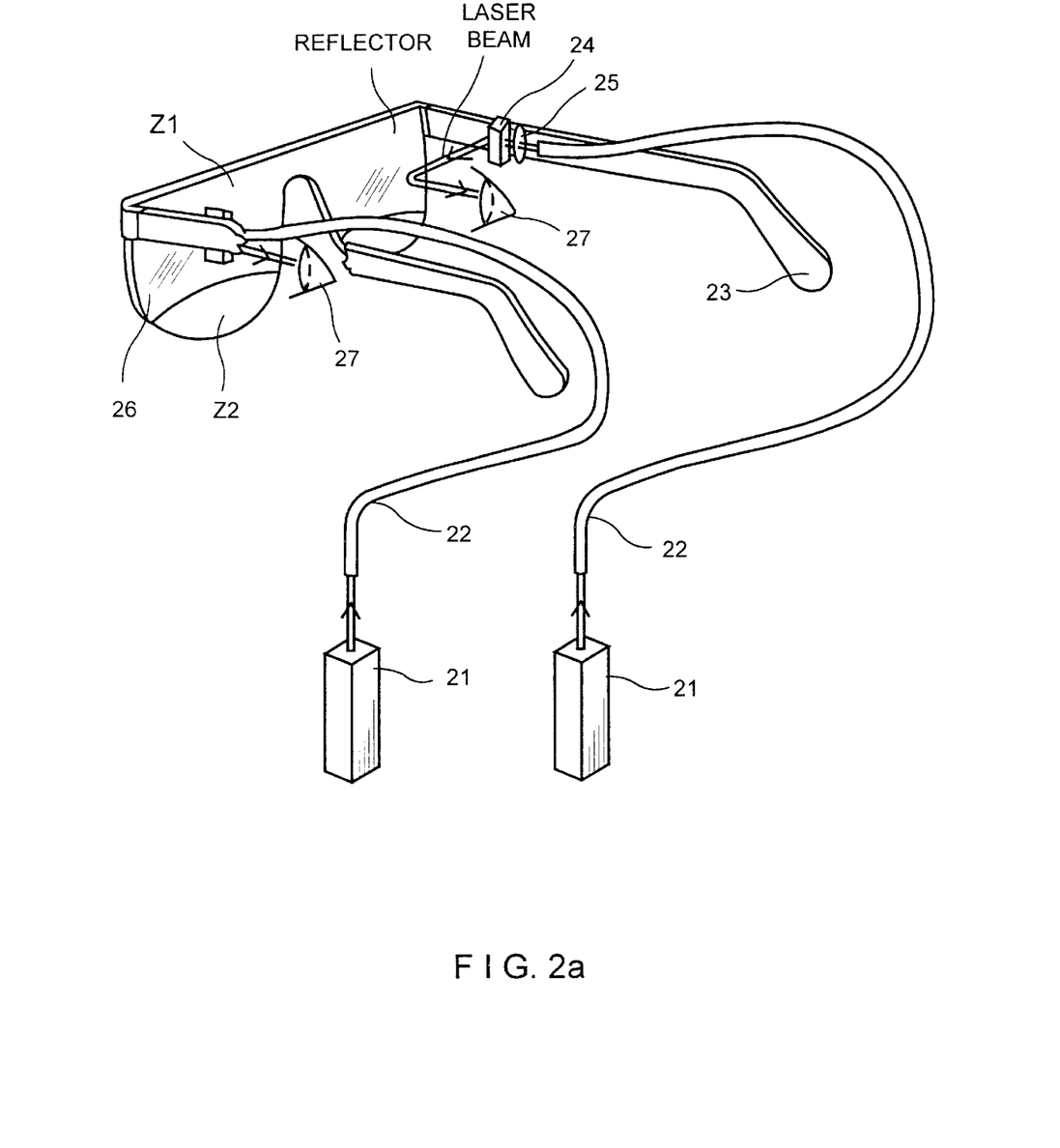
FIGS. 2a, b show a spectacle type frame for testing far vision and near vision.
Figure 2B:
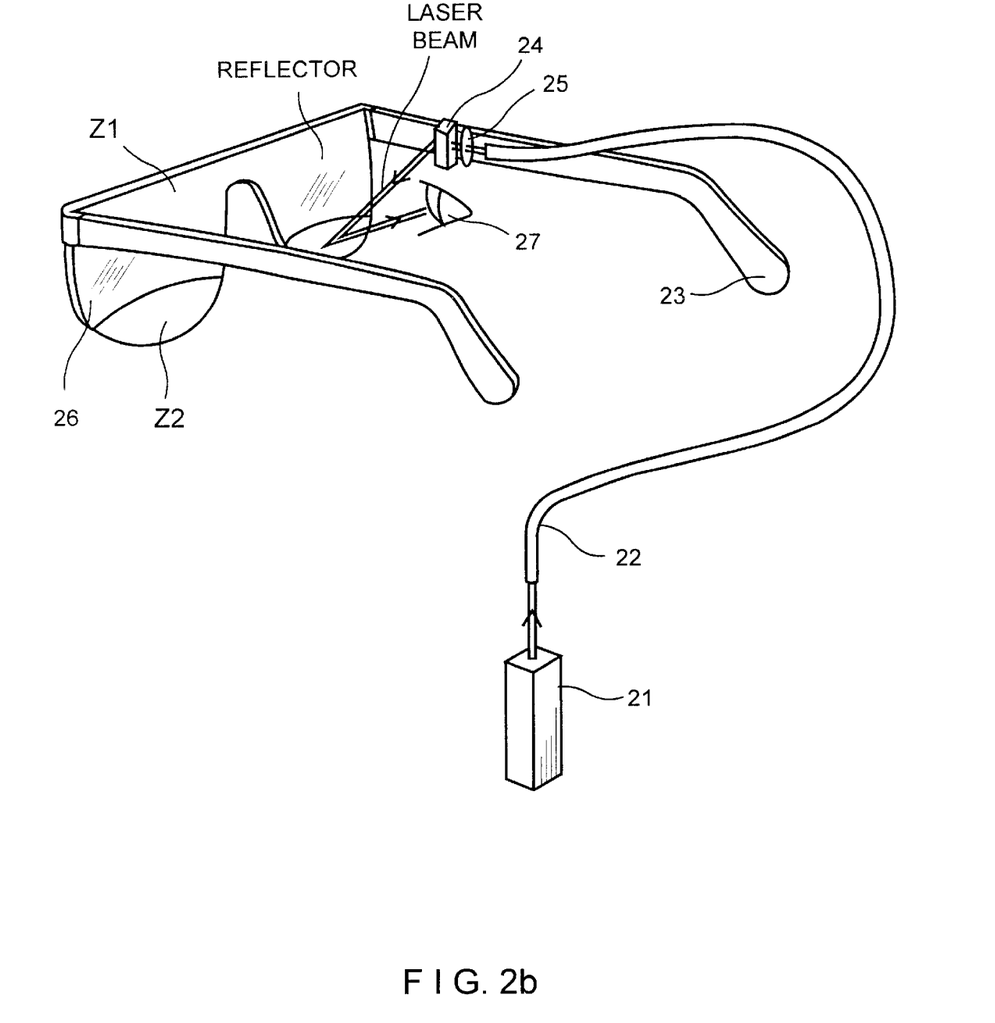

FIGS. 2a and 2b show laser light source 21, light guide 22, spectacle frame 23 and scanner 24 which is fastened to the spectacle frame 23, as well as a variable optical system 25, wherein the sequence of scanner 24 and optical system 25 can also be switched. The spectacle glasses 26 are advantageously semitransparent, i.e., the light distribution coming from the scanner 24 attached to the spectacle frame 23 is reflected by the spectacle glasses 26 but the surroundings can still be perceived. The reflective coating can also be wavelength-selective under certain circumstances.

In a particularly advantageous manner according to the invention, the spectacle glasses 26 are divided into at least a first, preferably flat, zone Z1 for far vision testing and at least a second zone Z2 for near vision testing which is preferably constructed as a concave mirror. The two zones Z1, Z2 can be constructed to be semitransparent.

The first zone Z1 projects the light distribution of the scanner 24 in the direction of the eye 27 without influencing it, while the second zone for the eye 27 effects a projection of the scanner image from a defined, non-infinite distance, e.g., from a distance of 40 cm. In this way, near vision testing can be performed according to the invention, wherein a viewing direction of the eye which is adapted to the natural near vision process is achieved by forming the second zone.

In order to change from the far vision area to the near vision area, the generated scan image is displaced downward by an angle α from the first zone to the second zone. This is effected either in that the scanning unit 24 is constructed such that it may be operated manually or by motor so as to be tiltable by the above angle or by means of a purposely controlled deflection of the scanner 24 within the projection area by darkening parts of the image or altered deflection of the vertical scanning element.

FIG. 2a contains a two-fold arrangement of light sources 21, light guides 22, scanners 24 and optics 25 in order to present images to both eyes 27 of the test subject simultaneously or alternately.

Particularly advantageous possibilities for determining subjective refraction are discussed hereinafter. By means of the system 25 constructed as variable optics, it is possible to purposely generate a convergence or divergence of the light projected onto the eye in an advantageous manner so that the far vision deficiency of the eye is compensated for based on information given by the patient in a reproducible and measurable manner, so that the test subject sees the image sharply.

As was already mentioned, both zones Z1, Z2 can be coated so as to be semitransparent so that a natural spatial impression and a relaxed viewing direction are made possible for the test subject. However, zones Z1 and Z2 can also be formed as a fully reflecting mirror.

Figure 3A:
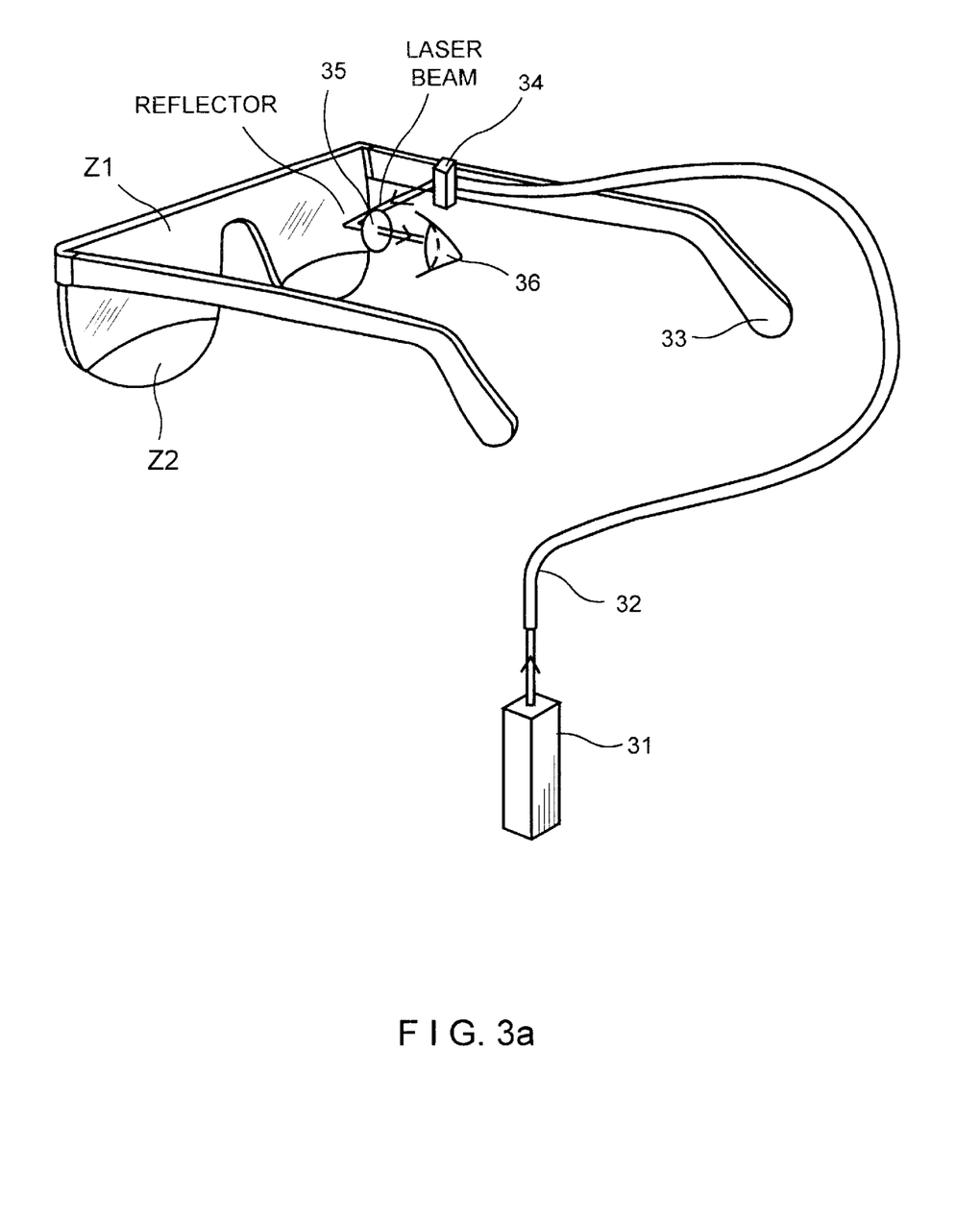
FIGS. 3a, b show a spectacle type frame with test glasses arranged in font of the eye.
Figure 3B:
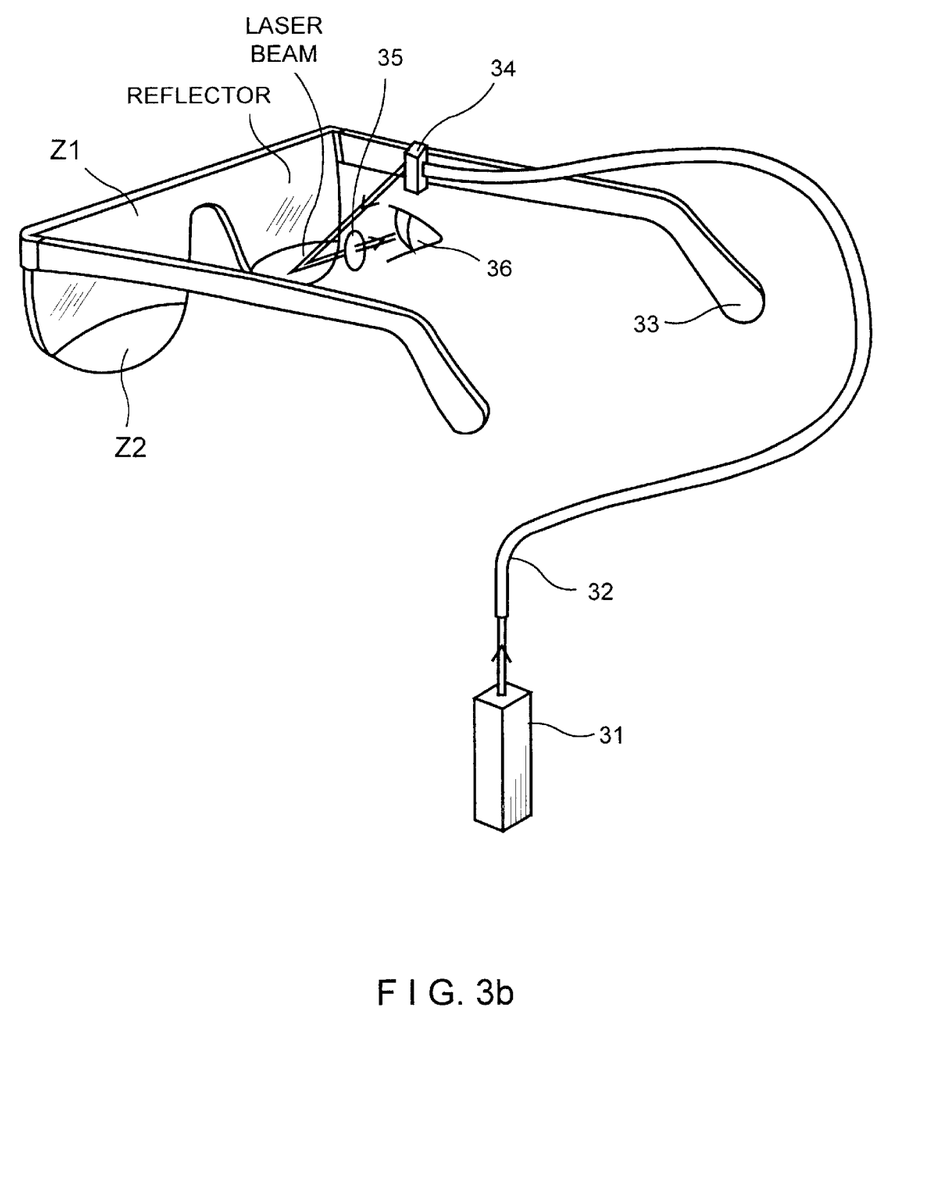

Further examination methods for deficient vision are explained hereinafter with reference to the schematic drawings shown in FIGS. 3a and 3b in that variable optical elements are arranged in front of the eye. In this case, light sources 31, light guides 32, a scanning unit 34 fastened to the spectacle frame 33, and exchangeable or variable elements 35 such as spherical lenses, cylindrical lenses, Stokes lenses, prismatic lenses, and prism compensators are arranged between zones Z1, Z2 of the spectacles and the eye 27 of the test subject. In FIG. 3a, for example, an optical element 35 of defined spherical and cylindrical effect is used in conjunction with zone Z1 and is supplemented in FIG. 3b by an add-on, not shown, with a positive action for near-vision testing in conjunction with zone Z2.

Figure 4A:
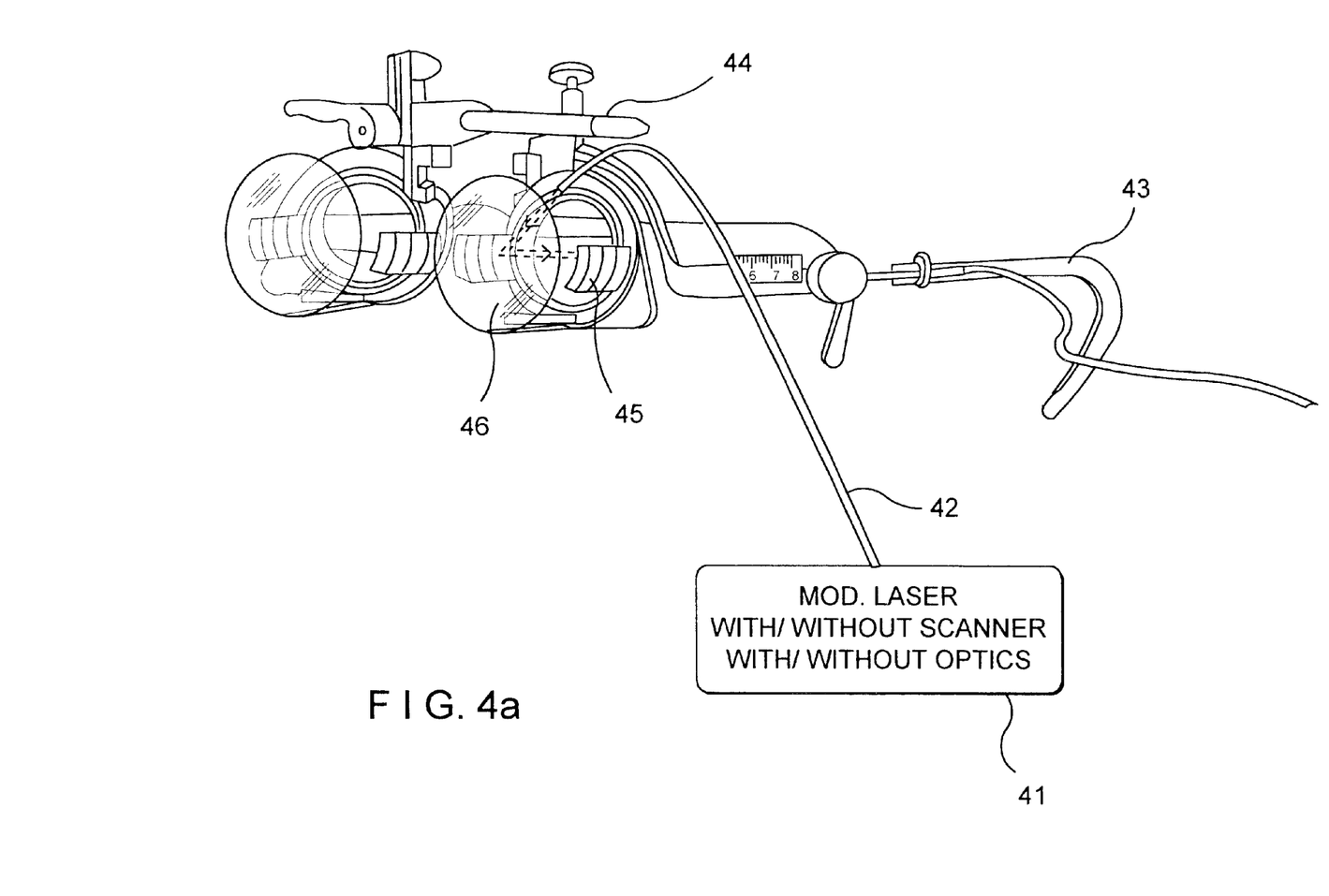
FIGS. 4a, b show the integration of the arrangement according to the invention in a trial frame or refraction spectacles.
Figure 4B:
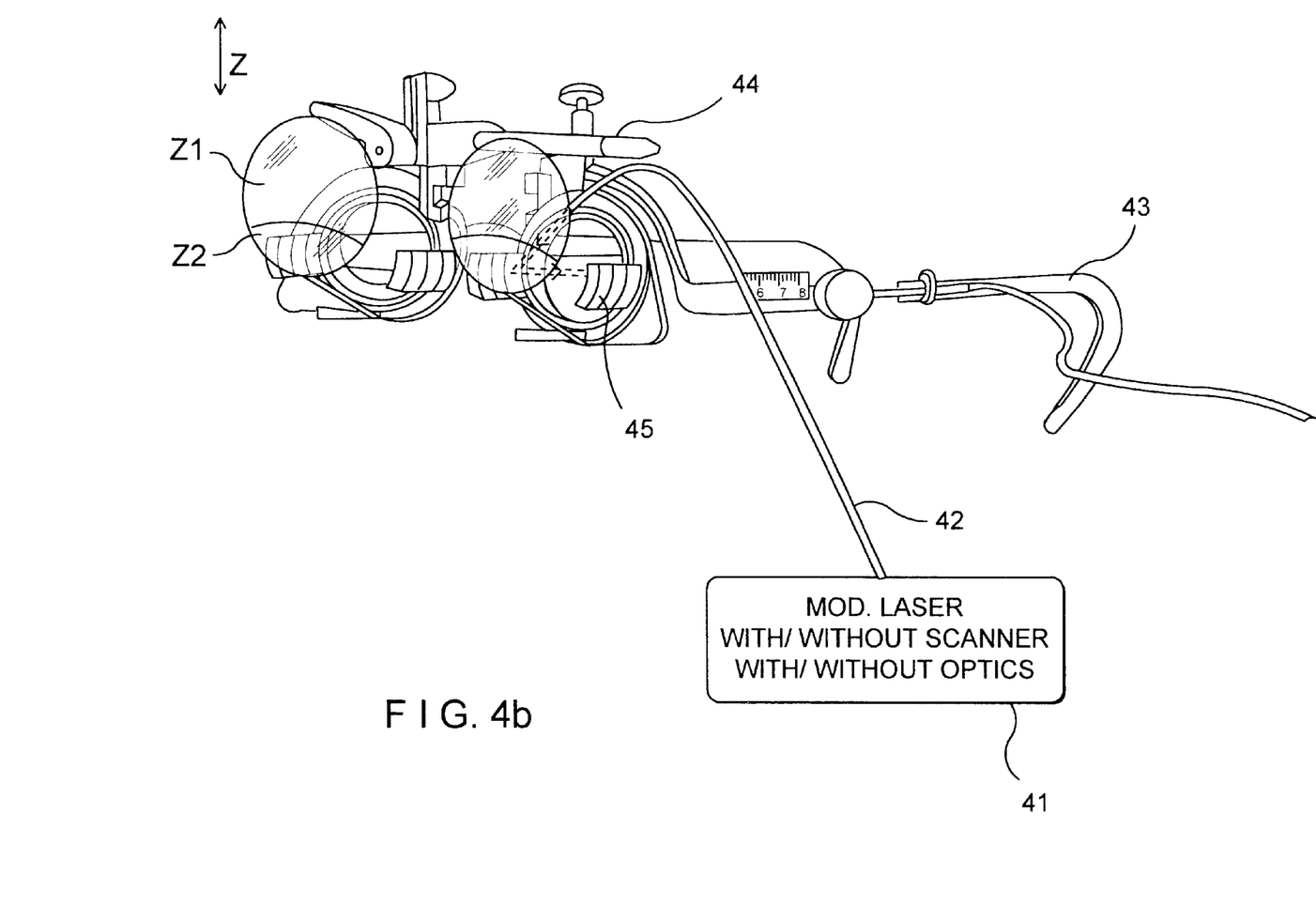

FIGS. 4a and 4b show the connection of the arrangement according to the invention in a schematic view with light source 41 (with scanner and optics), light guides 42, spectacle glass with reflector 46 with known refraction spectacles 44 on a common frame 43, wherein the refractive spectacles have holders for the use and exchange of test glasses 45.

Instead of the test spectacles 44, the invention can also work with the swivelable test glasses of a known phoropter arranged in front of the eye. In view of the fact that in such test spectacles or phoropters, the advantageous viewing direction of the test subject passes through the center of the test glasses, the spectacle glass 46, when divided into zones Z1, Z2 as in FIG. 4b, is advantageously put into different vertical positions as is shown schematically by the arrow in order to maintain this viewing direction for the different zones in far vision testing and near vision testing.

When using a spectacle glass 46 which is not divided into zones in arrangements according to FIGS. 2 to 5, a plane reflector can be used as spectacle glass and, as was mentioned above, an adjustment of the far vision area and near vision area can be effected by means of the variable optics arranged before or after the scanner.

Figure 5A:
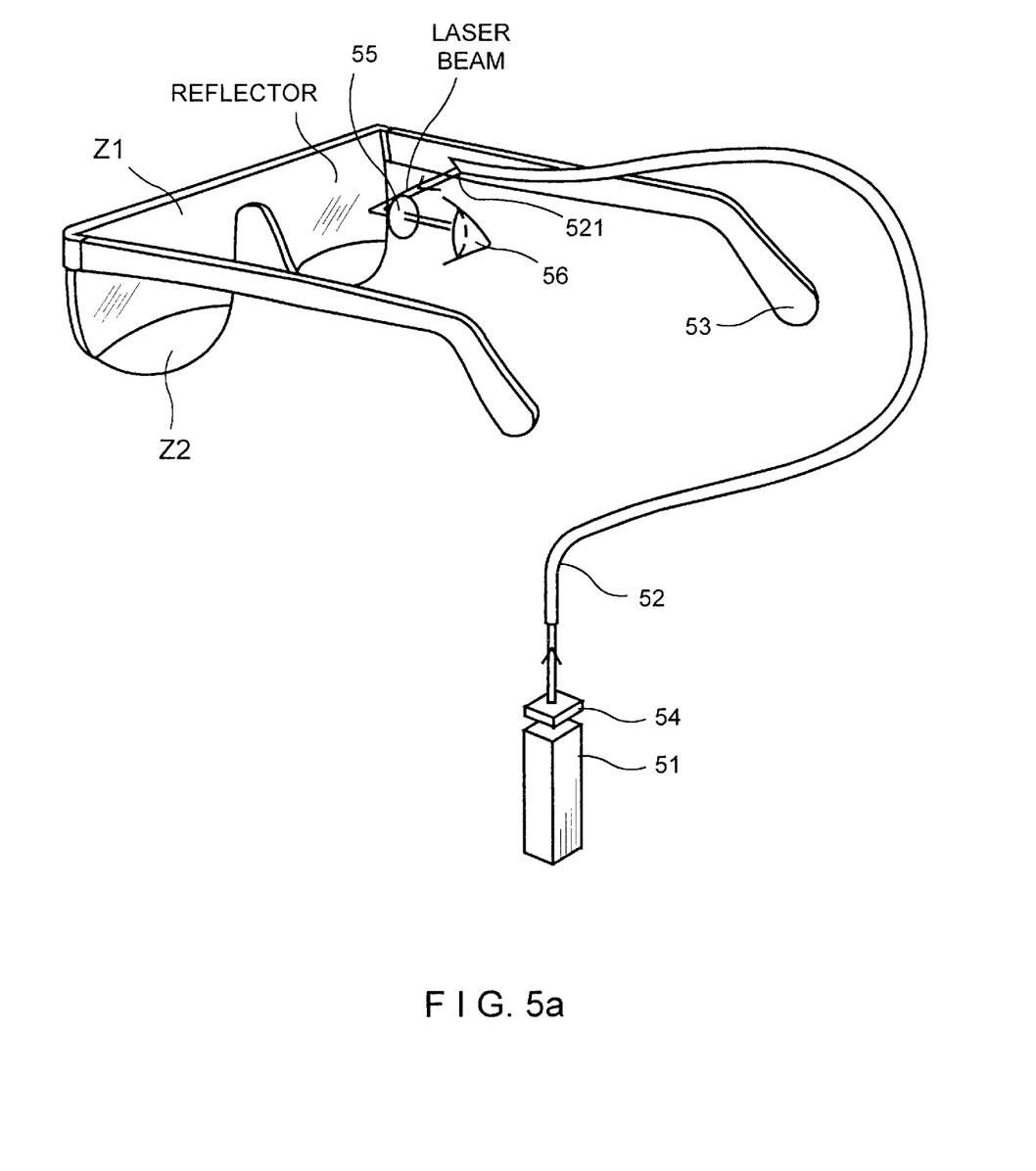
FIGS. 5a, b show an arrangement with a scanner arranged in front of the light guide.
Figure 5B:
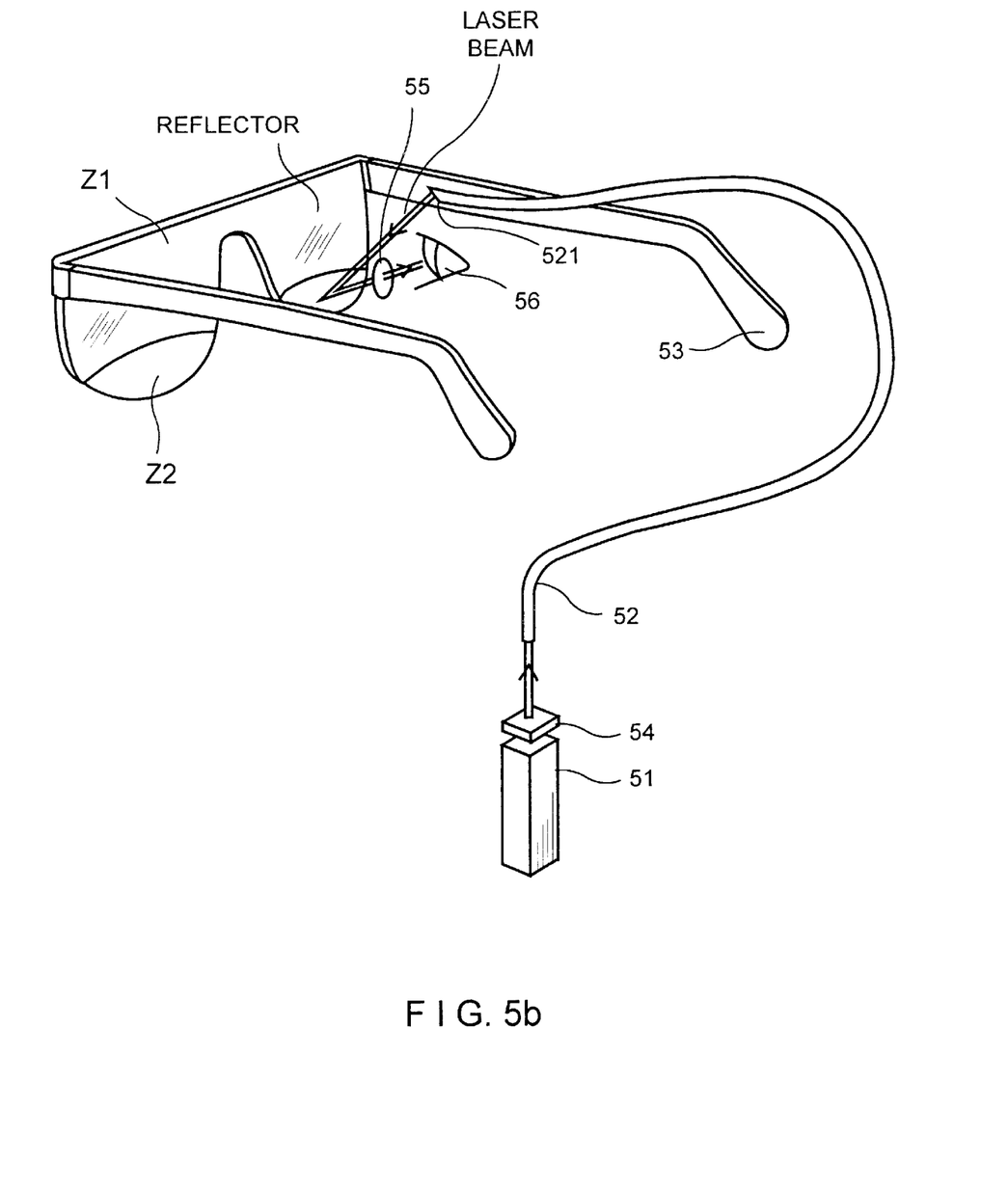

FIGS. 5a and 5b show the arrangement of the scanner 54 not on the spectacle frame 53, but rather following the light source 51 and prior to a flexible light guide 52, e.g., an image-carrying fiber bundle, leading to the spectacle frame 53, which arrangement is advantageous because it is lighter for the patient. The image generated by the scanner 54 is coupled into this flexible light guide 52, preferably in a known manner by means of optics, not shown, wherein projection is effected on the retina via alternating optical components 55, zones Z1, Z2, and the optical system of the eye 56 via the light guide end 521 fastened to the spectacle frame, optionally with variable optics following the latter. In a manner analogous to that described above, vision deficiency and other visual functions can also be determined with this system.

Further, the technical effect of the variable optics according to FIGS. 2a, 2b can also be transmitted into the area in front of the light guide input by arranging a variable optical system there.

Figure 6A:
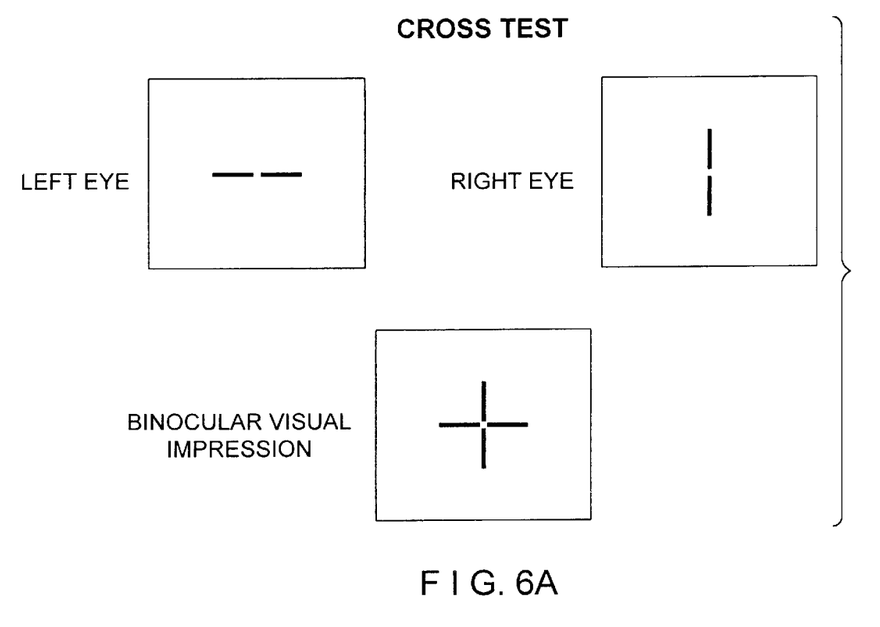
FIGS. 6a, b show a binocular test and a stereoscopic vision test.

FIG. 6a shows a binocular test such as that which can be realized with an arrangement according to the invention in that the partial images are displaced relative to one another in a defined manner corresponding to the information given by the test subject by suitably controlling the modulator or the horizontal and/or vertical scanning elements.

Figure 6B:
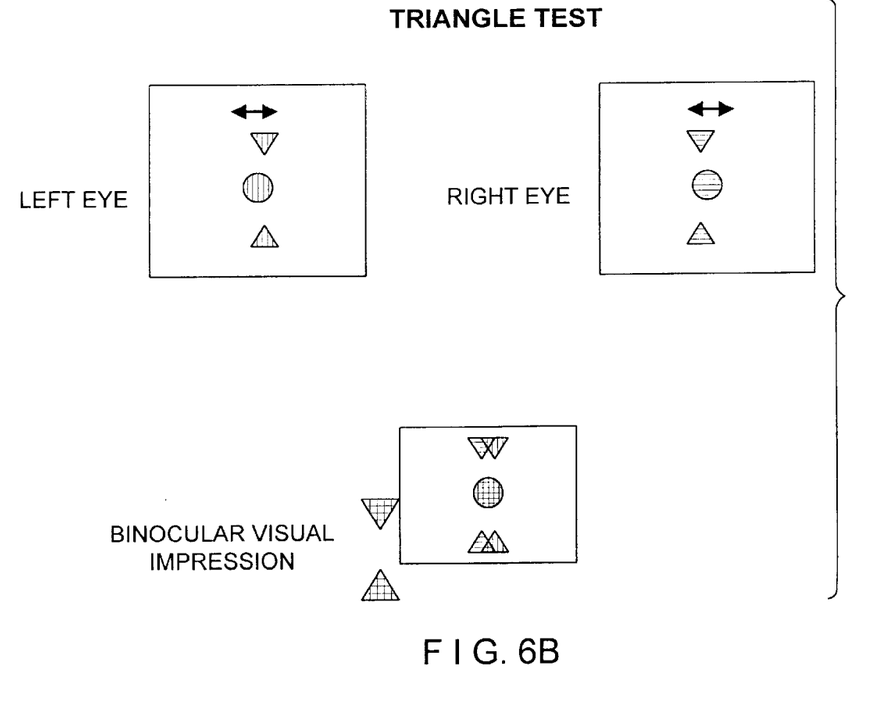

FIG. 6b shows a stereoscopic vision test, wherein the stereoscopic impression is altered by displaceable partial images.

Figure 7A:
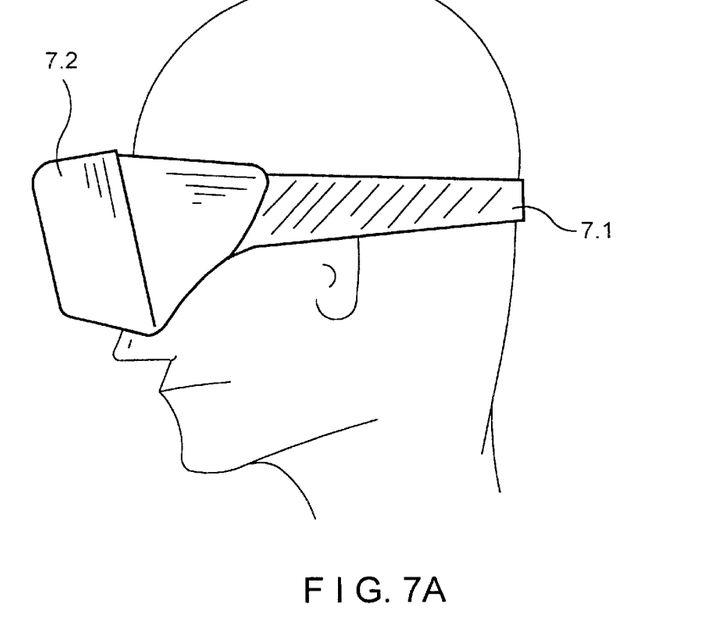
FIGS. 7a and 7b show a display for carrying out the invention attached to the head of the observer.
Figure 7B:
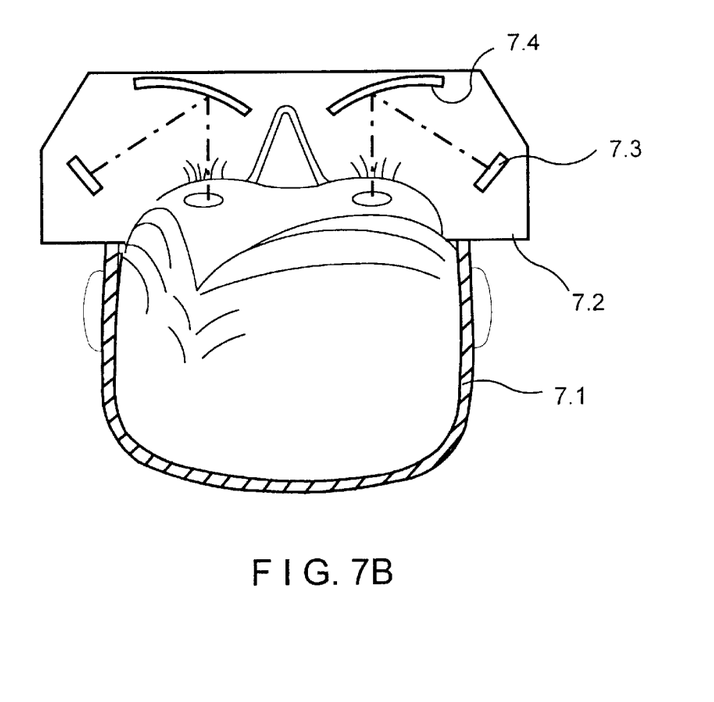

The different advantageous possibilities for determining vision functions were explained in the preceding with particular reference to an optical electronic system for direct projection on the retina. However, the described vision function tests can also be advantageously carried out by means of the spectacle type or helmet type frames mentioned in the beginning for monocular or binocular imaging of test images generated by screens via semitransparent or preferably relatively small full mirrors. In so doing, refraction can also be determined based on the information of the patent by means of intermediate optics which can be adjusted in a defined manner or exchanged. FIGS. 7a and 7b show a display 7.2 attached to the head of the observer, e.g., by means of a strap 7.1, wherein the image of two screens 7.3 is seen by the observer via suitable semitransparent or fully reflective deflecting elements 7.4.

While the foregoing description and drawings represent the present invention, it will be obvious to those skilled in the art that various changes may be made therein without departing from the true spirit and scope of the present invention.

What is claimed is:

1. An arrangement for projecting a two-dimensional image onto an eye to be examined for use with a device that determines subjective refraction and/or performs other visual functions, comprising:

at least one light source providing source light;

at least one light modulator for modulating the source light to produce modulated light;

a driving unit for controlling said modulator to modulate the source light in accordance with video information corresponding to a video image;

two-dimensional deflecting means for deflecting the modulated light to produce a two-dimensional image;

optical transmission means for optically transmitting the light of the light source, said optical transmission means being a light guide;

optical projection means for optically projecting the two-dimensional image onto a retina of an eye to be examined, the optical projection means projecting light to the two-dimensional deflecting means; and spectacles with partially or fully reflecting glasses, said optical transmission means being comprised of a flexible optical transmitter fastened on both sides to said spectacles, said optical projection means being said glasses, and said glasses reflecting the two-dimensional image onto the retina.

2. The arrangement according to claim 1, wherein the glasses of said spectacles are comprised of different reflective areas.

3. The arrangement according to claim 2, wherein the different areas of said glasses have either different curvature or at least one of said areas is curved and at least one of said areas is flat.

4. The arrangement according to claim 2, wherein a first of said areas is provided for far vision testing and a second of said areas is provided for near vision testing.

5. The arrangement according to claim 2, wherein a first of said areas is a plane mirror and a second of said areas is a concave mirror.

6. The arrangement according to claim 2, further comprising means for optically aligning the two-dimensional image on a selected area of the glasses of the spectacles.

7. The arrangement according to claim 1, further comprising swiveling means swivelably fastening the transmission means to the spectacles.

8. The arrangement according to claim 1, said arrangement further comprising moving means for moving the glasses in and out of a light path extending between the light guide and the eye being examined.

9. The arrangement according to claim 8, wherein said moving means is arranged between the glasses of the spectacle and the eye.

10. The arrangement according to claim 9, wherein spherical or cylindrical test glasses can be introduced and removed.

11. The arrangement according to claim 4, wherein said first area is an upper area and said second area is a lower area.

12. The arrangement according to claim 1, further comprising means for inserting test glasses within a frame of said spectacles.

13. An arrangement for projecting an image onto an eye to be examined for use with a device that determines refraction comprising:

at least one IR laser light source providing IR laser light;

at least one light modulator for modulating the IR laser light to produce modulated laser light;

a driving unit for controlling the modulator to modulate the IR laser light in accordance with video information corresponding to a video image;

two-dimensional deflecting means for deflecting the modulated laser light to produce a two-dimensional image;

optical transmission means for optically transmitting the light of the laser light source;

optical projection means for optically projecting the two-dimensional image onto a retina of an eye to be examined;

spectacles with glasses that entirely or partially reflect the IR light; and a receiver provided behind the glasses or on the glasses for receiving the IR light.

* * * * *